United States Patent [19]

Roscher et al.

[11] Patent Number: 5,744,010
[45] Date of Patent: Apr. 28, 1998

[54] PROCESS FOR THE PREPARATION OF THE NON-TOXIC SALTS OF 6-METHYL-3,4-DIHYDRO-1,2,3-OXATHIAZIN-4-ONE 2,2-DIOXIDE AND ARRANGEMENT FOR CARRYING OUT THIS PROCESS

[75] Inventors: Günter Roscher, Kelkheim; Heinz Litterer, Bad Schwalbach; Axel Engelmann, Königstein; Wolf-Dietmar Kaufmann, Kronberg; Bernd Laugwitz, Bad Soden; Hans-Dietmar Schnabel, Eppstein, all of Germany

[73] Assignee: Hoechst Aktiengesellschaft, Germany

[21] Appl. No.: 302,807

[22] PCT Filed: Mar. 16, 1993

[86] PCT No.: PCT/EP93/00606

§ 371 Date: Jun. 19, 1995

§ 102(e) Date: Jun. 19, 1995

[87] PCT Pub. No.: WO93/19055

PCT Pub. Date: Sep. 30, 1993

[30] Foreign Application Priority Data

Mar. 17, 1992 [DE] Germany .......................... 42 08 513.6

[51] Int. Cl.⁶ .................... B01D 11/00; C07D 291/00
[52] U.S. Cl. ........................... 203/43; 203/46; 203/98;
203/DIG. 16; 202/202; 202/204; 544/2;
549/355; 549/397; 549/463

[58] Field of Search ..................... 202/202, 204;
203/43, 46, 98, DIG. 16; 544/2; 549/463,
355, 397

[56] References Cited

U.S. PATENT DOCUMENTS

| | | | |
|---|---|---|---|
| 3,689,485 | 9/1972 | Clauss | 260/243 |
| 3,969,348 | 7/1976 | Pietsch et al. | 260/243 |
| 4,263,102 | 4/1981 | Schorr et al. | 203/22 |
| 4,289,586 | 9/1981 | Sabatka | 203/1 |
| 4,804,755 | 2/1989 | Reuschling et al. | 544/2 |

Primary Examiner—Nina Bhat
Attorney, Agent, or Firm—Connolly & Hutz

[57] ABSTRACT

The invention relates to a process for the preparation of acesulfam salts by reaction of salts of amidosulfonic acid with diketene to give a salt of acetoacetamidosulfonic acid (I), ring closure by the action of at least about an equivalent amount of $SO_3$, at least this ring closure reaction being carried out in the presence of a halogenated, aliphatic hydrocarbon as an inert solvent, treatment of the cyclization product with water and conversion of the resulting acesulfam-H (II) into the form of a non-toxic salt, which comprises, in the work-up by distillation of the resulting crude solvent, after removal of water and low-boilers and recovery of solvent sufficiently pure for reuse in the preparation of compounds (I) and/or (II), directly returning the remaining, solvent-containing distillation residue, without further purification, into the system downstream of the reaction vessel for carrying out the ring closure reaction.

20 Claims, 1 Drawing Sheet

PROCESS FOR THE PREPARATION OF THE NON-TOXIC SALTS OF 6-METHYL-3,4-DIHYDRO-1,2,3-OXATHIAZIN-4-ONE 2,2-DIOXIDE AND ARRANGEMENT FOR CARRYING OUT THIS PROCESS

6-Methyl-3,4-dihydro-1,2,3-oxathiazin-4-one 2,2-dioxide (hereafter acesulfam-H) has been used for some time in the form of its potassium salt (hereafter acesulfam-K)

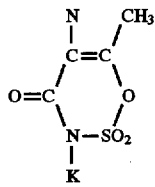

because of its intensive sweet taste as a sweetener in the food sector.

A series of different processes are known for the preparation of acesulfam-K (see inter alia Angewandte Chemie, 22(1973), pages 965 to 973). Of particular current interest is a process in which, in a solvent, preferably methylene chloride, amidosulfonic acid, but preferably a soluble salt of amidosulfonic acid, is first reacted with diketene to form the acetoacetamido compound. The salts of amidosulfonic acid used are generally alkaline metal salts or ammonium salts, preferably trialkylammonium salts. In the reaction with diketene, the salt of acetoacetamidosulfonic acid (I) is formed in accordance with the reaction equation $$NH_2-SO_3M + CH_2=C-O \atop \phantom{NH_2-SO_3M+CH_2=} | \phantom{xx} | \atop \phantom{NH_2-SO_3M+} CH_2-CO \quad (I)$$

$$CH_3-CO-CH_2CONH-SO_3M$$

(M=base cation, in particular HN(alkyl $C_1$–$C_6)_3$). The acetoacetamido compound (I) preferably dissolved in methylene chloride is then reacted under defined reaction conditions with a solution of $SO_3$, preferably in methylene chloride, and thus cyclized; the $SO_3$ is preferably used in excess (see for this EP-A 155,634, EP-A 159,516, EP-A 217,076 and EP-A 218,076). A cyclization product is formed in this manner, from which by reaction with water (hydrolysis) in a hydrolysis vessel, acesulfam-H, the so-called "sweetener acid" (II), is formed:

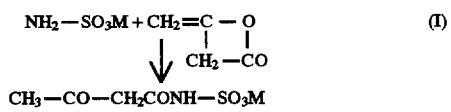

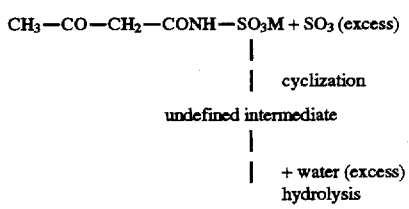

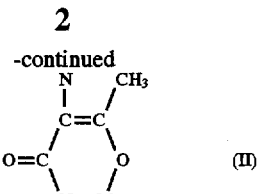

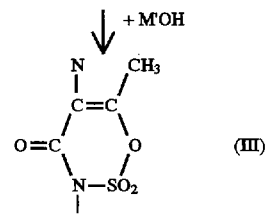

acesulfam-H ("sweetener acid")

↓ +M'OH acesulfam salt (acesulfam-K)
(M' = base cation, preferably K)

Both the cyclization and the hydrolysis are rapid, highly exothermic reactions.

The reaction mixture separates into an organic phase, preferably a methylene chloride phase, and an aqueous sulfuric acid phase. The majority (about ⅘) of the sweetener acid (II) is situated in the organic phase, about ⅕ is dissolved in the sulfuric acid phase. The sulfuric acid phase contains almost the entire amount of the alkali metal or ammonium, preferably trialkylammonium, as sulfate, preferably trialkylammonium hydrogen sulfate. The sulfuric acid phase, after stripping off any solvent still present, preferably methylene chloride, can be further utilized in another place. The isolation of the sweetener acid in the form of the desired salt (III) is expediently carried out by the method described in the abovementioned EP-A 218,076. In this, the sweetener acid contained in the sulfuric acid phase is first extracted therefrom in an extraction vessel using a solvent, preferably methylene chloride. The solvent used here is combined with the normal solvent phase which contains the majority of the sweetener acid. The small amount of sulfate dissolved in the solvent phase is then extracted from the combined solvent phases using only a little water in an extraction vessel and returned with the extraction water to react the cyclization product with water in the hydrolysis vessel to form sweetener acid. The sweetener acid is extracted from the remaining, substantially sulfate-free solution of the sweetener acid in the solvent, in the form of the desired salt, preferably the potassium salt, using aqueous alkali metal hydroxide solution, preferably potassium hydroxide solution. The aqueous solution of the sweetener (III) can be worked up by conventional methods, for example by evaporation or precipitation using external solvents, to give the pure crystalline sweetener (III).

The remaining solvent is water-saturated and contains a large part of the by-product formed in the reaction, such as acetone, trialkylamine and trialkylammonium salt of the sweetener acid when the trialkylamnonium salt of amidosulfonic acid was used, undefined high boilers and dissolved resins.

The solvent thus contaminated cannot be reused in this form. Thus in the mixing of the $SO_3$ in the cyclization stage with the contaminants, dark-colored solid insoluble compounds are formed which lead to blockages in the piping. In addition, with acetone, colored secondary products occur which pass through to the sweetener solution. A colorless sweetener can no longer be isolated from such solutions. Neither can this contaminated solvent be used in the preparation of the acetoacetamido compound (I) from the salt of amidosulfonic acid and diketene, since the yield of acetoacetamido compound decreases and highly colored by-products are formed. These are carried over into the sweetener solution obtained later and prevent the isolation of colorless solid acesulfam salt (III) from the solution.

The solvent used for the mixing with $SO_3$ and for the preparation of the acetoacetamido compound must therefore contain only small amounts of contaminants. The recovery of pure solvent from the crude solvent which is produced downstream of the neutralization of the sweetener acid in the form of its salt requires complex apparatus with a considerable energy consumption, since, for reasons of yield and the limited solubility of the sweetener acid in the solvent, only highly dilute solutions can be employed in the synthesis. The concentration of the sweetener acid, for example, in the methylene chloride solution which then passes on to the neutralization with the alkali metal hydroxide solution is generally only about 2 to 3% by weight. Therefore, in the purification by distillation of the crude solvent to recover pure reusable solvent, with consideration of the reflux ratios required, up to 100 kilograms of solvent must be evaporated per kilogram of prepared sweetener.

In the methods conventional hitherto, the purification of the solvent is carried out in more than two distillation columns. The bottom product of the last column, which contains trialkylamine, higher boiling components such as acetone, undefined high boilers, solid residues such as resins and small amounts of the salt of the sweetener acid and still about 70% solvent as solubilizer for the solid residues, must be incinerated. A further evaporation, i.e. a continuing recovery of solvent, is not possible since otherwise encrustations of solids occur which lead to mechanical faults.

In view of the disadvantages of this known process, the object was therefore in particular to provide a method for the preparation of acesulfam salts which permits a simpler recovery of the solvent used from the crude solvent with the use of at most two columns and at least substantially avoids the incineration of the resulting by-product and residues.

A process has now been found by which the discarding of solvent-containing bottom streams is avoided and which additionally permits carrying out the solvent recovery to give pure solvent, suitable for the preparation of the acetoacetamido compound (I) and for the preparation of the $SO_3$ mixture, in, optionally, one or at most two distillation columns, dispensing with a special distillation column for the removal of high boilers and residues.

The present invention therefore relates to a process for the preparation of acesulfam salts by reaction of salts of amidosulfonic acid with diketene to give a salt of acetoacetamidosulfonic acid (I), ring closure by the action of at least about an equimolar amount of $SO_3$, at least this ring closure reaction being carried out in the presence of a halogenated, aliphatic hydrocarbon as an inert solvent, treatment of the cyclization product (of the organic phase) with water and conversion of the resulting acesulfam-H (II) into the form of a non-toxic salt (III), which comprises, in the work-up by distillation of the resulting crude solvent, after removal of water and low-boilers and recovery of solvent sufficiently pure for reuse in the preparation of compounds (I) and/or (II), directly returning the remaining, solvent-containing distillation residue, without further purification, into the system downstream of the reaction vessel for carrying out the ring closure reaction.

Figure 1:
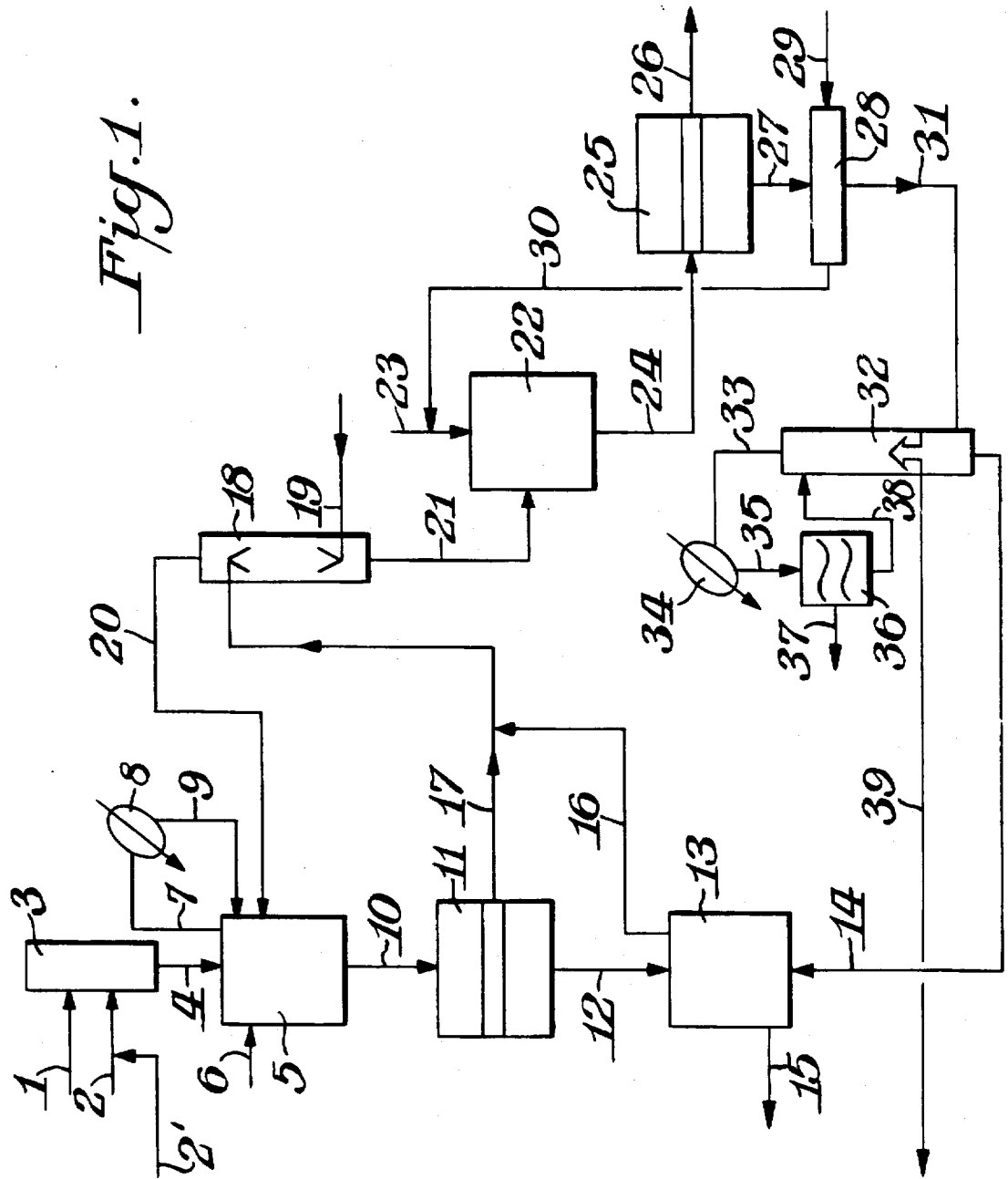
FIG. 1 illustrates the device for preparing the nontoxic salts according to this invention.

This solvent-containing distillation residue is preferably returned to the vessel for treating the organic phase with water (hydrolysis vessel (5)), into the phase separation vessel (11) and/or into the extraction vessel (13); see FIG. 1 below for this.

The preparation of the acesulfam salt, preferably acesulfam-K (III), is carried out in a manner known per se as described in the abovementioned EP-A 155,634, EP-A 159,516, EP-A 217,024 and EP-A 218,076, which are referred to here. Accordingly, the acetoacetamido compound (I) is first prepared by reaction of, preferably, a salt of amidosulfonic acid, in particular the trialkylammonium salt, at temperatures of generally 0° to 100° C., preferably 20° to 45° C., with diketene in an inert solvent, preferably likewise a halogenated, aliphatic hydrocarbon, in particular methylene chloride. The ring closure reaction is then carried out using $SO_3$, which is preferably used in a more than equimolar amount, to give an $SO_3$ adduct as an unisolated intermediate, the solvent used being preferably the same as that in the first stage, in particular methylene chloride. The temperatures here are generally between −20° and 40° C., preferably −10° and 15° C. This $SO_3$ adduct is then hydrolyzed to give the sweetener acid (II), the temperatures here being generally 20° to 50° C., preferably 35° to 45° C. This sweetener acid is then converted by a suitable alkali metal hydroxide solution, preferably potassium hydroxide solution, in a neutralization stage into a non-toxic salt (III), preferably the potassium salt.

The halogenated, aliphatic hydrocarbons used as solvent are preferably those having up to 4 carbon atoms which form an azeotrope with water, such as methylene chloride, chloroform, 1,2-dichloroethane, trichloroethylene, tetrachloroethylene, trichlorofluoroethylene etc., methylene chloride being particularly preferred.

In a preferred embodiment of the invention, the same solvent, preferably methylene chloride, is used both for the salt of acetoamido-N-sulfonic acid (I) and for $SO_3$.

Although the molar ratio of acetoacetamido-N-sulfonate (I) to $SO_3$ can be about 1:1, a one to about 20-fold $SO_3$ excess is preferred, preferably about a 3- to 10-fold, in particular about a 4- to 7-fold molar excess.

In the preferred case of the use of salts of acetoacetamido-N-sulfonic acid (I) and $SO_3$ in a molar ratio of 1 to more than 1, an "$SO_3$ adduct" is formed in the ring closure reaction, from which the acesulfam-H (II) must be set free by hydrolysis. This hydrolysis is carried out by addition of water or ice and/or addition of dilute aqueous sulfuric acid, expediently in about a 2- to 6-fold molar amount, in relation to the $SO_3$ excess used. For this hydrolysis, both water and dilute aqueous sulfuric acid are preferably used, which dilute aqueous sulfuric acid originates from the downstream extractor (18) and generally has a concentration of 2 to 20% by weight.

After the hydrolysis, a 2- or (if acesulfam-H has already precipitated) 3-phase mixture is then present. The acesulfam-H (II) is present essentially dissolved in the organic phase and in the sulfuric acid phase. The organic phase is then removed. The organic phase removed from the aqueous sulfuric acid phase, or the corresponding combined organic phases, are, preferably, then purified by extraction with water in the extractor (18) mentioned above, the sulfuric acid contained therein being first extracted from the organic phase.

The volume ratio of the organic phase to the aqueous extraction phase is generally about (20-5):1. However, even with substantially smaller amounts of water, an effective purification can still be achieved.

The extraction is carried out in the simplest case by stirring the two phases in a stirred flask or in a stirred tank; special apparatuses which are useful are, in principle, all industrial extraction apparatuses such as mixer-settlers, sieve-plate columns, packed columns, Karr columns etc. Mixing elements such as static mixers can also be used to intensify the contact of the extraction phases.

The proportion of acesulfam-H extracted simultaneously with the sulfuric acid is generally, depending on the water amount used, between about 2 and 30% of the total acesulfam-H contained in the organic phase. For the economic efficiency of the overall process, it is important to return the water phase to the hydrolysis of the "$SO_3$ adduct".

The non-toxic salts (III) of the acesulfam-H are recovered from the purified organic phase or the purified combined organic phases by neutralization with bases. Bases which are useful here are those having non-toxic cations. Preference is given to potassium bases (solutions of KOH, $KHCO_3$, $K_2CO_3$), in particular KOH.

The neutralization of acesulfam-H and the recovery of non-toxic salts thereof from this acesulfam-H-containing purified organic phase is advantageously carried out by intensive contact of the purified organic, phase, or of the corresponding combined organic phases, with aqueous alkali metal hydroxide solution. The intensive contact is generally carried out in the manner of an extraction by the processes conventional therefor in the conventional apparatuses as have already been described above. Mixing elements, such as static mixers, can also be used here.

In the neutralization, sufficient base is generally used so that the aqueous phase achieves a pH of about 5 to 12, preferably about 8 to 11. The acesulfam salt is then recovered from the aqueous phase in a conventional manner (by crystallization).

According to a preferred embodiment, the work-up of the solvent, preferably methylene chloride, by distillation is carried out in one distillation column only. According to a further preferred embodiment, the solvent-containing distillation residue is returned to the system at more than one point, in particular to the phase separation vessel (11) and/or the extraction vessel (13).

A further preferred embodiment provides that the salt of acetoacetamidosulfonic acid (I) used is trialkylammonium acetoacetamidosulfonate, dissolved in methylene chloride, the ring closure is carried out by the action of a more than equimolar amount of $SO_3$, if desired, likewise in methylene chloride as solvent, the undefined cyclization product produced as an $SO_3$ adduct after the ring closure reaction is hydrolyzed in a hydrolysis vessel to form acesulfam-H, a separation is carried out in downstream phase separation vessel into an organic phase and aqueous sulfuric acid-containing phase, this aqueous phase is then extracted in an extraction vessel with methylene chloride and this methylene chloride, together with the organic phase from the phase separation vessel is fed to a further extractor for washing out sulfuric acid residues and sulfate residues using water, the non-toxic salts of acesulfam-H are recovered, by neutralization using bases, from the organic phase thus purified and a separation into aqueous salt solution and a methylene chloride phase is carried out in a downstream phase separation vessel, and this methylene chloride phase is fed, if desired via at least one further extraction stage, to the distillation column.

The work-up and recovery of the solvent (methylene chloride) is preferably carried out in the context of the process according to the invention in such a manner that the crude solvent is introduced into a distillation column in the bottom thereof or above the bottom thereof, the distillation residue, which in addition to parts of the solvent, contains solid by-products and high-boilers, is withdrawn from this distillation column and returned to the system, preferably to the hydrolysis vessel (5), the phase separation vessel (11) and/or the extraction vessel (13) for extraction of the sulfuric acid phase, water, small amounts of the solvent and any low-boilers which may be present with this are withdrawn at the head of this distillation column, while the majority of the solvent is returned as reflux to the distillation column, and sufficiently purified solvent is withdrawn from the central part of the column from an intermediate plate which is located beneath the reflux and above the feed of crude solvent into the column and this purified solvent is returned into the system, preferably into the reaction vessel for the preparation of compounds (I) and/or (II) and for the preparation of the $SO_3$ solution. Obviously, part of this purified solvent, which generally contains at most 2% by weight, preferably at most 1% by weight, and, in particular, only 0.9 to 0.1% by weight of contaminants, can also be used in the following points of the system.

The process according to the invention offers surprising advantages. Thus, the complexity of the apparatus is significantly less, since only one column or at most two columns are required instead of three columns. In addition, no solvent-containing residues are produced, the disposal (incineration) of which would require additional special devices. Furthermore, the energy consumption for purification by distillation of the crude solvent is lower.

The practicability of the process according to the invention was surprising, since on return of the by-products, such as acetone and polymeric solids, into the system, a concentration in the total circulation was to be expected which would finally pass through to the end product (acesulfam salt (K) solution). Contaminants in the acesulfam salt (K) solution, which is further worked up to give pure solid acesulfam salt (K), make the recovery thereof in pure form more difficult or impossible if highly colored polymers are present in the solution.

Furthermore, it was to be expected that the solvent withdrawn from the intermediate plate in the distillation column described would contain significantly more water than was actually found; however, the water content in the solvent discharged from the intermediate plate was surprisingly significantly lower than in the bottom and the head of the column.

The present invention further relates to an arrangement for carrying out the process according to the invention, essentially comprising the reaction vessel (3) for carrying out the cyclization reaction from the compounds (I) and $SO_3$, a downstream hydrolysis vessel (5) for the recovery of the sweetener acid (II), a phase separation vessel (11) connected thereto for the separation of the organic phase and the sulfuric acid phase, preferably an extractor (13) for the extraction of the isolated sulfuric acid phase using the solvent, preferably a further extractor (18) for the extraction of the organic phases combined from (11) and (13) using water, a neutralization vessel (22) for the conversion of the sweetener acid (II) into the corresponding salt (III), a phase separation vessel (25) for the separation of the aqueous solution of the salt (III) from the solvent and a distillation column (32).

A phase separation vessel (36) is preferably connected to the distillation column (32), into which phase separation vessel the vapor condensate passes over from the column head and is here separated into an aqueous phase and a solvent phase. The latter is returned into the column. Pure solvent is withdrawn from an intermediate plate of the column, which generally has 15 to 50, preferably 20 to 30, theoretical plates. The solvent-containing distillation residue is preferably returned from the column bottom into the hydrolysis vessel (5), into the phase separation vessel (11) and/or into the extraction vessel (13). This distillation residue generally still contains at least 10% by weight, preferably 50 to 98% by weight and, in particular, 75 to 95% by weight or solvent.

The process according to the invention is now described by way of example with reference to FIG. 1:

Via line (1), a solution of $SO_3$ in methylene chloride is fed to the reaction vessel (mixer) (3); the feed of acetoacetamido trialkylammonium salt solution in methylene chloride is carried out via line (2) into the reaction vessel (3). Additional methylene chloride is added to this solution via line (2') for dilution. The heat of reaction is removed via evaporation of part of the methylene chloride, evaporating methylene chloride and liquid product passing together via line (4) to the vessel (5) furnished with the stirrer. Water is fed to the vessel (5) via the line (6); the heat of reaction of the hydrolysis (hydration) step is also removed via methylene chloride evaporation. The methylene chloride vapors pass via line (7) to the condenser (8); the condensate returns via line (9) to the vessel (5). The liquid mixture in vessel (5) passes via line (10) to the phase separation vessel (11). The lower sulfuric acid phase of the vessel (11) is passed via line (12) to the extractor (mixer-settler vessel) (13), in which this sulfuric acid phase is stirred with methylene chloride from line (14) for the extraction of the sweetener acid. The sulfuric acid phase is withdrawn from the extractor (13) via line (15). The methylene chloride loaded with sweetener acid leaves vessel (13) via Line (16). The methylene chloride phase from the phase separation vessel (11) is withdrawn via line (17) and is transported with the methylene chloride from line (16) to the extractor (18). Water is fed to the extractor (18) for the extraction of dissolved sulfate below via line (19), which water, after leaving the extractor (18), is conducted via line (20) to the hydrolysis vessel (5). The methylene chloride phase of the extractor (18) is conducted via line (21) to the stirred neutralization vessel (22), to which aqueous potassium hydroxide solution is passed via line (23), the rate of which is controlled via the pH in the stirred vessel (22). The mixture is conducted via line (24) to the phase separation vessel (25). The upper phase is aqueous acesulfam-K solution, which is withdrawn via line (26). The lower methylene chloride phase is conducted via line (27) to the mixer-settler vessel (28), in which it is washed with a little water which is added to the mixer-settler (28) via line (29). The washing water is conducted via line (30) together with the aqueous potassium hydroxide solution to the neutralization vessel (22). The methylene chloride phase withdrawn from the mixer-settler (28) is crude methylene chloride which is passed via line (31) into the bottom of the distillation column (32). The vapors from the column (32) pass via line (33) to the condenser (34) and the two-phase condensate passes via the line (35) to the phase separation vessel (36). The aqueous phase separating in the phase separation vessel (36) is withdrawn via line (37); the methylene chloride phase is returned via line (38) as reflux into column (32). The by-product-containing methylene chloride is withdrawn at the bottom of column (32) via line (14) for the extraction of the sweetener acid from sulfuric acid in extractor (13). Pure methylene chloride is taken off from an intermediate plate situated in the column via line (39), which pure methylene chloride is reused for the $SO_3$ mixture and/or to prepare the trialkylammonium acetoacetamidosulfonate solution.

Comparison Example 1

Only pure fresh methylene chloride is employed without reprocessing. The rates given are per hour.

A solution of 11.0 kg of $SO_3$ in 46.0 kcg of methylene chloride at a temperature of +5° C. is fed via line (1) to the reaction vessel (3). 15.0 kg of methylene chloride solution at 0° C., which contains 6.6 kg of triethylammonium acetoacetamidosulfonate and 1.0 kg of polymeric components of different composition and unreacted starting material in a small amount are introduced into the reaction vessel (3) via line (2). This solution is diluted with 12.0 kg of methylene chloride via line (2'). The preparation of the solution is carried out in a stainless steel stirred tank by the introduction of 10.0 kg of methylene chloride, addition of 2.5 kg of amidosulfonic acid, 2.8 kg of triethylamine, 0.1 kg of acetic acid and then careful addition of 2.2 kg of diketene after the above components have completely dissolved. The mixture formed in the reaction vessel, which contains a not precisely definable cyclization product as a solution in methylene chloride, by-products formed and methylene chloride evaporated by the heat of reaction, is fed via line (4) to the so-called hydrolysis vessel (5) (stirred tank).

8.0 kg of water are added via line (6) to the hydrolysis tank (5). 20.0 kg of the methylene chloride evaporated by the heat of reaction pass via line (7) to the condenser (8), while the condensate returns via line (9) to the stirred tank (5). The liquid mixture in hydrolysis tank (5), which is held in a constant state, is conducted via line (10) to the phase separator (11). The lower sulfuric acid phase flows via line (12) to the mixer-settler (13). 30.0 kg of pure fresh methylene chloride are conveyed via line (14) to the mixer-settler (13). 26.0 kg of sulfuric acid phase are withdrawn via line (15). This sulfuric acid phase contains 41% sulfuric acid, 31% water, 21% triethylammonium hydrogen sulfate, 0.5% acetic acid, 1% acetone, 0.1% sweetener acid, 3% undefined organic compounds and 1% dissolved methylene chloride. Via line (16), the methylene chloride phase is passed from the mixer-settler (13) into line (17). 100.5 kg of methylene chloride phase are withdrawn from the phase separator (11) via line (17) which contain, in addition to other components, 0.2% water, 2.4% sweetener acid and 0.4% sulfate. The combined methylene chloride streams from the lines (16) and (17) are fed to the extractor (18). 2.7 kg of water are introduced at the bottom of the extractor via line (14); the extraction water is returned via line (20) to the hydrolysis tank (5). The methylene chloride phase of the extractor (18) is fed via line (21) to the neutralization vessel (22) (stirred tank, water cooling in outer jacket); approximately 10% strength potassium hydroxide solution is transported via line (23) into the tank (22) with pH control to pH 9 in the tank (22). The resulting two-phase mixture is conducted via line (24) to the phase separator (25). The lower methylene chloride phase is fed from the phase separator (25) via line (27) to the mixer-settler (28) in which this methylene chloride phase is washed using 6.4 l of water via line (29). The washing water passes, together with the potassium hydroxide solution, via line (30) to the neutralization vessel (22).

99.0 kg of methylene chloride are withdrawn via line (31). The methylene chloride contains 0.15% water, 0.1% triethylamine, 0.4% acetone and 0.5% polymers.

17.6 kg of acesulfam-K solution are withdrawn as the upper phase of the phase separator (25) via line (26). The light-yellow solution contains 1% methylene chloride, 17% acesulfam-K, 0.3% potassium sulfate and 0.5% acetone, 0.1% triethylamine and <0.5% unknown compounds.

On evaporation of this sweetener solution to approximately 30% of the original volume, cooling and filtration, colorless acesulfam-K is obtained as a solid.

Comparison Example 2

Feed of crude methylene chloride to the reaction by dilution of the triethylammonium acetoaceteamido sulfonate solution with crude instead of pure methylene chloride.

The experimental arrangement and rates are as in Comparison Example 1, but to dilute the acetoacetamido compound in line (2), instead of pure methylene chloride, dilution is carried out via line (2') using 12.0 kg of crude methylene chloride from line (31) in Comparison Example 1.

On evaporation of the acesulfam-K solution obtained via line (26), which solution is now dark-colored, in correspondence with Comparison Example 1, yellow acesulfam-K is obtained as a solid which can only be obtained in a colorless form via redissolution and further treatment of the solution using adsorbents.

Example 3

The experimental arrangement is as in the comparison examples. However, the crude methylene chloride from the mixer-settler (28) is now conducted via line (31) into the bottom of the distillation column (32) for reprocessing. 99.0 kg of crude methylene chloride are introduced via line (31) into the bottom of the column (32) (45 sieve plates, intermediate plate for liquid withdrawal at plate 30).

The crude methylene chloride corresponds in the composition to the crude methylene chloride in Comparison Example 1; the other individual streams also initially correspond to the individual streams of Comparison Example 1.

The bottom heating of column (32) is regulated so that 110.0 kg of distillate are produced via vapor line (32) in the condenser (34) (cooling:cold water), which distillate is conducted via line (35) to the phase separator (36). 0.13 kg of water phase are withdrawn via line (37). The lower organic methylene chloride phase is returned via line (38) as reflux into the column. 66.0 kg of pure methylene chloride are withdrawn at the intermediate plate via line (39). This methylene chloride contains, as contaminant, 140 ppm of water, 40 ppm of acetone, <30 ppm of triethylamine; it is reused as solvent for the preparation of the acetoacetamido compound and for the dilution of the solution prior to the reaction and for the preparation of the $SO_3$ solution.

29.7 kg of material are withdrawn from the bottom of column (32) via line (14) which are used for the extraction of the sweetener acid from the sulfuric acid phase in the mixer-settler (13) and are returned via line (16) to the methylene chloride phase via line (17).

The bottom material from the column (32) in line (14) is essentially composed of methylene chloride which contains 300 ppm of water, 1.4% of acetone, 0.3% of triethylamine and 1.7% of polymers.

After an experimental duration of several clays, when all individual streams are in concentration equilibrium, the bottom stream (14) shows a slight increase in acetone concentration to 2%, but a concentration of the polymers or other components does not occur. The sulfuric acid withdrawn contains 2% acetone, 0.5% condensation products of the acetone, 5% polymers and undefined organic compounds. 17.6 kg of acesulfam-K solution are withdrawn via line (26); the light-yellow solution contains 17% acesulfam-K, 1% methylene chloride, 0.3% potassium sulfate, 0.6% acetone, 0.1% triethylamine, <0.5% unknown compounds. On evaporation of this solution to 30% of the original volume, cooling and filtration, colorless acesulfam-K is obtained as a solid.

In principle, an identical result is obtained if the bottom product of column (32) is fed to the hydrolysis vessel (5). In this case, for example, head product of column (32) can also be used for the extraction of the sweetener acid from the sulfuric acid phase in vessel (13). The phase separator (32) is not necessarily required in this variant.

We claim:

1. A process for preparation of acesulfam, in acid or salt form, by cyclization of an acetoacetamidosulfonate salt, comprising the following steps:

(a) cyclization of the acetoacetamidosulfonate salt with $SO_3$ in a reaction zone containing a halogenated, aliphatic hydrocarbon solvent, to obtain a $SO_3$ adduct in said solvent, (b) downstream from said reaction zone, treating said $SO_3$ adduct, in said solvent, with an aqueous medium, to obtain 6-methyl-3,4-dihydro-1,2,3-oxathiazin-4-one2, 2-dioxide and neutralizing the resulting solution of 6-methyl-3,4-dihydro-1,2,3-oxathiazin-4-one2,2-dioxide in said solvent, (c) downstream from said reaction zone, distilling the resulting solvent from step (b) to recover purified solvent sufficiently pure for use in the preparation of an acetoacetamidosulfonate salt or 6-methyl-3,4-dihydro-1,2,3-oxathiazin-4-one2,2-dioxide and solvent-containing residue of the distillation, (d) introducing said solvent-containing residue, without further purification, into a step of said process, downstream from said reaction zone.

2. The process as claimed in claim 1, wherein the process contains at most two distillation columns.

3. The process as claimed in claim 1, wherein the solvent used is methylene chloride.

4. The process as claimed in claim 1, wherein the work-up by distillation is carried out in only one distillation column.

5. The process as claimed in claim 1, wherein the solvent-containing distillation residue is returned to at least one of the following: a vessel for carrying out said treatment of the cyclization product with water, a phase separation vessel downstream therefrom or an extraction vessel downstream therefrom.

6. The process as claimed in claim 1, wherein the salt of acetoacetamidosulfonic acid used is trialkylammonium acetoacetamidosulfonate, the ring closure is the result of the reaction of a more than equimolar amount of $SO_3$, the $SO_3$ adduct produced after the ring closure reaction is hydrolyzed in a hydrolysis vessel to give acesulfam-H, a separation is carried out in downstream phase separation vessel into an organic phase and aqueous sulfuric acid-containing phase, this aqueous phase is then extracted in an extraction vessel with methylene chloride and this methylene chloride, together with the organic phase from the phase separation vessel is fed to a further extractor for washing with water, the non-toxic salts of 6-methyl-3,4-dihydro-1,2,3-oxathiazin-4-one2,2-dioxide are recovered, by neutralization using bases, from the organic phase thus purified and a separation into aqueous salt solution and a methylene chloride phase is carried out in a downstream phase separation vessel, and this methylene chloride phase is fed, optionally via at least one further extraction stage, to the distillation column.

7. The process as claimed in claim 6, wherein the solvent-containing distillation residue is returned into an extractor, provided downstream of the treatment of the cyclization product with water, for the extraction of the acesulfam, in acid or salt form, still present in the aqueous phase.

8. The process as claimed in claim 1, wherein the crude solvent is introduced into a distillation column in the bottom thereof or above the bottom thereof, the solvent containing residue is withdrawn from said distillation column and returned into the vessel for the treatment of the cyclization product, the phase separation vessel which is located downstream of said distillation column and/or the extraction vessel is used for extraction of the sulfuric acid phase, water, small amounts of the solvent and any low-boilers which are present with this are withdrawn at the head of this distillation column, while the major amount of the solvent is returned as reflux to the distillation column, and sufficiently purified solvent is withdrawn from the central part of the column from an intermediate plate which is located beneath the reflux and above the feed of crude solvent into the column and this purified solvent is returned into the system.

9. The process as claimed in claim 8, wherein the purified solvent is sufficiently pure for use in the rind closure and is returned to a reaction vessel for the ring closure.

10. The process as claimed in claim 1, wherein the solvent-containing distillation residue is returned into a vessel for carrying out the treatment of the cyclization product with water.

11. The process as claimed in claim 1, wherein the distillation residue from the distillation column still contains at least 10% by weight of solvent.

12. An apparatus for carrying out the process of claim 1, comprising a reaction vessel (3) for carrying out a cyclization reaction with a salt of acetoacetamidosulfonic acid (I) and $SO_3$ in an organic solvent, a downstream hydrolysis vessel (5) for the recovery of sweetener acid (II), the hydrolysis resulting in the formation of an organic phase containing 6-methyl-3,4-dihydro-1,2,3-oxathiazin-4-one 2,2-dioxide and a sulfuric acid phase, a first phase separation vessel (11) connected thereto for the separation of the organic phase and the sulfuric acid phase, a neutralization vessel (22) for the conversion of the 6-methyl-3,4-dihydro-1,2,3-oxathiazin-4-one 2,2-dioxide into a corresponding salt thereof, means for conveying said organic phase containing 6-methyl-3,4-dihydro-1,2,3-oxathiazin-4-one 2,2-dioxide to said neutralization vessel, and, receiving the effluent from said neutralization vessel, a second phase separation vessel (25) for the separation of said effluent into an organic solvent phase and an aqueous solution phase, the aqueous solution containing said corresponding salt and a distillation column (32) in communication with said second phase separation vessel (25) for distilling the organic solvent phase.

13. The apparatus as claimed in claim 12, wherein a phase separation vessel (36) is connected to the distillation column (32), into which phase separation vessel the condensed vapors pass from the head of said distillation column and in which a separation is carried out into an aqueous phase and a solvent phase.

14. The apparatus as claimed in claim 12, wherein the distillation column (32) has 15 to 50 theoretical plates.

15. The apparatus as claimed in claim 12, wherein said apparatus further comprises a means for conveying organic solvent phase, without further purification, from the bottom of distillation column (32) to a point upstream of the distillation column, the means for conveying organic solvent from the bottom of the distillation column is disposed upstream of the distillation column (32) and located downstream of the reaction vessel (3).

16. A process as claimed in claim 15, comprising:

e. prior to said distilling step, separating the effluent, from said treating of said $SO_3$ adduct with the aqueous medium, into an organic, solvent-containing phase and a sulfuric acid phase in a separation zone, f. subsequent to said step e but prior to said distilling step, extracting acesulfam from said sulfuric acid phase in an extraction zone.

17. The apparatus as claimed in claim 12, which further comprises a first extractor (13) for extracting acesulfam from said sulfuric acid phase, the extraction medium for this first extractor being said organic solvent, and a second extractor (18) for extraction of a combination of the organic phases obtained from the phase separation vessel (11) and the first extractor (13), the extraction medium for the second extractor being water.

18. A process as claimed in claim 16, wherein said solvent-containing residue, without further purification, is directly conveyed to said separation zone.

19. A process as claimed in claim 16, wherein said solvent-containing residue, without further purification, is directly conveyed to said extraction zone to serve as the extraction medium for extracting acesulfam from said sulfuric acid phase.

20. A process for preparation of acesulfam, in acid or salt form, by cyclization of an acetoacetamidosulfonate salt, comprising the following steps:

a. cyclization of the acetoacetamidosulfonate salt with $SO_3$ in a reaction zone containing a halogenated, aliphatic hydrocarbon solvent, to obtain an $SO_3$ adduct in said solvent, b. downstream from said reaction zone, treating said $SO_3$ adduct, in said solvent, with an aqueous medium, to obtain 6-methyl-3,4-dihydro-1,2,3-oxathiazin-4-one-2,2-dioxide and neutralizing the resulting solution of 6-methyl-3,4-dihydro-1,2,3-oxathiazin-4-one-2,2dioxide in said solvent, thereby contaminating said solvent, c. downstream from said reaction zone, distilling the resulting contaminated solvent to recover:
purified solvent sufficiently pure for use in the preparation of a an acetoacetamidosulfonate salt or 6-methyl-3,4-dihydro-1,2,3-oxathiazin-4-one2,2-dioxide, and
solvent-containing residue of the distillation, d. introducing said solvent-containing residue, without further purification, into a step of said process, downstream from said reaction zone.

* * * * *